US007780701B1

(12) United States Patent
Meridew et al.

(10) Patent No.: US 7,780,701 B1
(45) Date of Patent: Aug. 24, 2010

(54) SUTURE ANCHOR

(75) Inventors: Jason D Meridew, Columbia City, IN (US); Ryan A Kaiser, Leesburg, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1585 days.

(21) Appl. No.: 10/640,216

(22) Filed: Aug. 13, 2003

(51) Int. Cl.
*A61B 17/04* (2006.01)
(52) U.S. Cl. ............................. 606/232; 606/139
(58) Field of Classification Search ......... 606/228–232, 606/72–79, 220, 139, 104, 300, 301, 65, 606/67, 144–148; 411/394, 407–412
See application file for complete search history.

(56) References Cited

U.S. PATENT DOCUMENTS

| 734,204 A | 7/1903 | Voss |
|---|---|---|
| 838,203 A | 12/1906 | Neil |
| 2,121,193 A | 6/1938 | Hanicke |
| 2,268,755 A | 1/1942 | Li |
| 2,329,398 A | 9/1943 | Duffy |
| 3,003,155 A | 10/1961 | Mielzynski et al. |
| 3,845,772 A | 11/1974 | Smith |
| 3,892,232 A | 7/1975 | Neufeld |
| 4,275,717 A | 6/1981 | Bolesky |
| 4,409,974 A | 10/1983 | Freedland |
| 4,454,875 A | 6/1984 | Pratt et al. |
| 4,496,468 A | 1/1985 | House et al. |
| 4,532,926 A | 8/1985 | O'Holla |
| 4,632,100 A | 12/1986 | Somers et al. |
| 4,641,652 A | 2/1987 | Hutterer et al. |
| 4,653,486 A | 3/1987 | Coker |
| 4,669,473 A | 6/1987 | Richards et al. |
| 4,738,255 A | 4/1988 | Goble et al. |
| 4,741,330 A | 5/1988 | Hayhurst |
| 4,776,328 A | 10/1988 | Frey et al. |
| 4,779,616 A | 10/1988 | Johnson |
| 4,836,205 A | 6/1989 | Barrett |
| 4,895,148 A | 1/1990 | Bays et al. |
| 4,898,156 A | 2/1990 | Gatturna et al. |
| 4,899,743 A | 2/1990 | Nicholson et al. |
| 4,946,468 A | 8/1990 | Li |

(Continued)

FOREIGN PATENT DOCUMENTS

EP          0 260 970 A2       3/1988

(Continued)

OTHER PUBLICATIONS

Arthrex, Corkscrew Suture Anchors, 1998, p. 105.

(Continued)

*Primary Examiner*—Anhtuan T Nguyen
*Assistant Examiner*—Kathleen Sonnett
(74) *Attorney, Agent, or Firm*—Harness, Dickey

(57) ABSTRACT

A resorbable suture anchor operable to hold a suture within a bone. The suture anchor has a cannulated tip that receives a driver during implantation of the anchor, the driver extending from the tip when the anchor is seated on the driver. The anchor further has at least one engagement surface to prevent migration of the anchor from the implantation site. The anchor is made of a resorbable material to permit resorbtion of the anchor within a patient at a desired rate.

10 Claims, 6 Drawing Sheets

U.S. PATENT DOCUMENTS

| | | | |
|---|---|---|---|
| 4,968,315 A | 11/1990 | Gatturna | |
| 4,994,074 A | 2/1991 | Bezwada et al. | |
| 5,002,550 A | 3/1991 | Li | |
| 5,019,080 A | 5/1991 | Hemer | |
| 5,037,422 A | 8/1991 | Hayhurst et al. | |
| 5,041,129 A | 8/1991 | Hayhurst et al. | |
| 5,064,425 A | 11/1991 | Branemark et al. | |
| 5,100,417 A | 3/1992 | Cerier et al. | |
| 5,120,171 A | 6/1992 | Lasner | |
| 5,122,132 A | 6/1992 | Bremer | |
| 5,127,785 A | 7/1992 | Faucher | |
| 5,141,520 A | 8/1992 | Goble et al. | |
| 5,156,616 A | 10/1992 | Meadows et al. | |
| D331,463 S | 12/1992 | Rosenberg et al. | |
| 5,176,682 A | 1/1993 | Chow | |
| 5,207,679 A | 5/1993 | Li | |
| 5,224,946 A * | 7/1993 | Hayhurst et al. | 606/72 |
| 5,246,441 A | 9/1993 | Ross et al. | |
| 5,258,016 A | 11/1993 | DiPoto et al. | |
| 5,364,400 A * | 11/1994 | Rego et al. | 606/72 |
| 5,370,662 A | 12/1994 | Stone et al. | |
| 5,372,146 A | 12/1994 | Branch | |
| 5,374,270 A | 12/1994 | McGuire et al. | |
| 5,417,712 A | 5/1995 | Whittaker et al. | |
| 5,423,860 A | 6/1995 | Lizardi et al. | |
| 5,431,660 A | 7/1995 | Burke | |
| 5,443,482 A | 8/1995 | Stone et al. | |
| 5,472,452 A | 12/1995 | Trott | |
| 5,520,700 A | 5/1996 | Beyar et al. | |
| 5,522,845 A | 6/1996 | Wenstrom, Jr. | |
| 5,524,946 A | 6/1996 | Thompson | |
| 5,527,342 A | 6/1996 | Pietrzak et al. | |
| D374,287 S | 10/1996 | Goble et al. | |
| D374,482 S | 10/1996 | Goble et al. | |
| 5,562,672 A | 10/1996 | Huebner et al. | |
| 5,573,548 A | 11/1996 | Nazre et al. | |
| 5,584,695 A | 12/1996 | Lal Sachdeva et al. | |
| 5,584,835 A | 12/1996 | Greenfield | |
| 5,593,425 A | 1/1997 | Bonutti et al. | |
| 5,601,557 A | 2/1997 | Hayhurst | |
| 5,607,432 A | 3/1997 | Fucci | |
| 5,618,314 A | 4/1997 | Harwin et al. | |
| 5,643,320 A | 7/1997 | Lower et al. | |
| D385,352 S | 10/1997 | Bales et al. | |
| 5,681,352 A | 10/1997 | Clancy, III et al. | |
| 5,683,401 A | 11/1997 | Schmieding et al. | |
| 5,683,418 A | 11/1997 | Luscombe et al. | |
| 5,690,676 A * | 11/1997 | DiPoto et al. | 606/232 |
| 5,720,766 A | 2/1998 | Zang et al. | |
| 5,733,307 A | 3/1998 | Dinsdale | |
| 5,743,914 A | 4/1998 | Skiba | |
| 5,814,070 A | 9/1998 | Borzone et al. | |
| 5,851,219 A | 12/1998 | Goble et al. | |
| 5,868,789 A | 2/1999 | Huebner | |
| 5,885,294 A | 3/1999 | Pedlick et al. | |
| 5,911,721 A | 6/1999 | Nicholson et al. | |
| RE36,289 E * | 8/1999 | Le et al. | 606/232 |
| 5,951,560 A | 9/1999 | Simon et al. | |
| 5,957,953 A | 9/1999 | DiPoto et al. | |
| 5,964,783 A | 10/1999 | Grafton et al. | |
| 5,968,044 A | 10/1999 | Nicholson et al. | |
| 5,980,558 A * | 11/1999 | Wiley | 606/232 |
| 6,045,573 A | 4/2000 | Wenstrom, Jr. et al. | |
| 6,059,785 A | 5/2000 | Schavan et al. | |
| 6,096,060 A | 8/2000 | Fitts et al. | |
| 6,117,162 A | 9/2000 | Schmieding et al. | |
| 6,139,565 A | 10/2000 | Stone et al. | |
| 6,146,406 A * | 11/2000 | Shluzas et al. | 606/232 |
| 6,159,235 A | 12/2000 | Kim | |
| 6,168,598 B1 | 1/2001 | Martello | |
| 6,214,031 B1 | 4/2001 | Schmieding et al. | |
| 6,231,606 B1 | 5/2001 | Graf et al. | |
| 6,264,677 B1 | 7/2001 | Simon et al. | |
| 6,287,324 B1 | 9/2001 | Yarnitsky et al. | |
| 6,319,270 B1 | 11/2001 | Grafton et al. | |
| 6,355,043 B1 | 3/2002 | Adam | |
| 6,436,124 B1 | 8/2002 | Anderson et al. | |
| 6,508,830 B2 * | 1/2003 | Steiner | 606/232 |
| 6,517,542 B1 | 2/2003 | Papay et al. | |
| 6,524,316 B1 | 2/2003 | Nicholson et al. | |
| 6,592,609 B1 * | 7/2003 | Bonutti | 606/232 |
| 6,656,183 B2 * | 12/2003 | Colleran et al. | 606/232 |
| 6,673,094 B1 * | 1/2004 | McDevitt et al. | 606/232 |
| 6,685,728 B2 * | 2/2004 | Sinnott et al. | 606/232 |
| 6,692,507 B2 * | 2/2004 | Pugsley et al. | 606/153 |
| 6,840,953 B2 * | 1/2005 | Martinek | 606/232 |
| 7,214,232 B2 | 5/2007 | Bowman et al. | |
| 2001/0037131 A1 | 11/2001 | Schmieding et al. | |
| 2002/0120292 A1 | 8/2002 | Morgan | |
| 2002/0147463 A1 | 10/2002 | Martinek | |
| 2002/0161401 A1 | 10/2002 | Steiner | |
| 2003/0125743 A1 * | 7/2003 | Roman et al. | 606/72 |

FOREIGN PATENT DOCUMENTS

| | | |
|---|---|---|
| FR | 2 606 270 A1 | 5/1988 |
| GB | 2 118 474 A | 11/1983 |
| WO | WO 86/03666 | 7/1986 |
| WO | WO 89/01767 | 3/1989 |
| WO | WO 89/10096 | 11/1989 |
| WO | WO 93/14705 | 8/1993 |

OTHER PUBLICATIONS

Bionx Implants, Duet Suture Anchor, 1 page.
ID Innovasive Devices, Inc., Soft Tissue Repair System, 1995, 2 pages.
Mitek Products, Division of ETHICON, Inc., a Johnson & Johnson company, Cuff Tack Sutureless Fixation Device, 2001, 2 pages.
Surgical Dynamics, A subsidiary of the United States Surgical Corporation, S-D-sorb Suture Anchor System, 1997, 1 page.

* cited by examiner

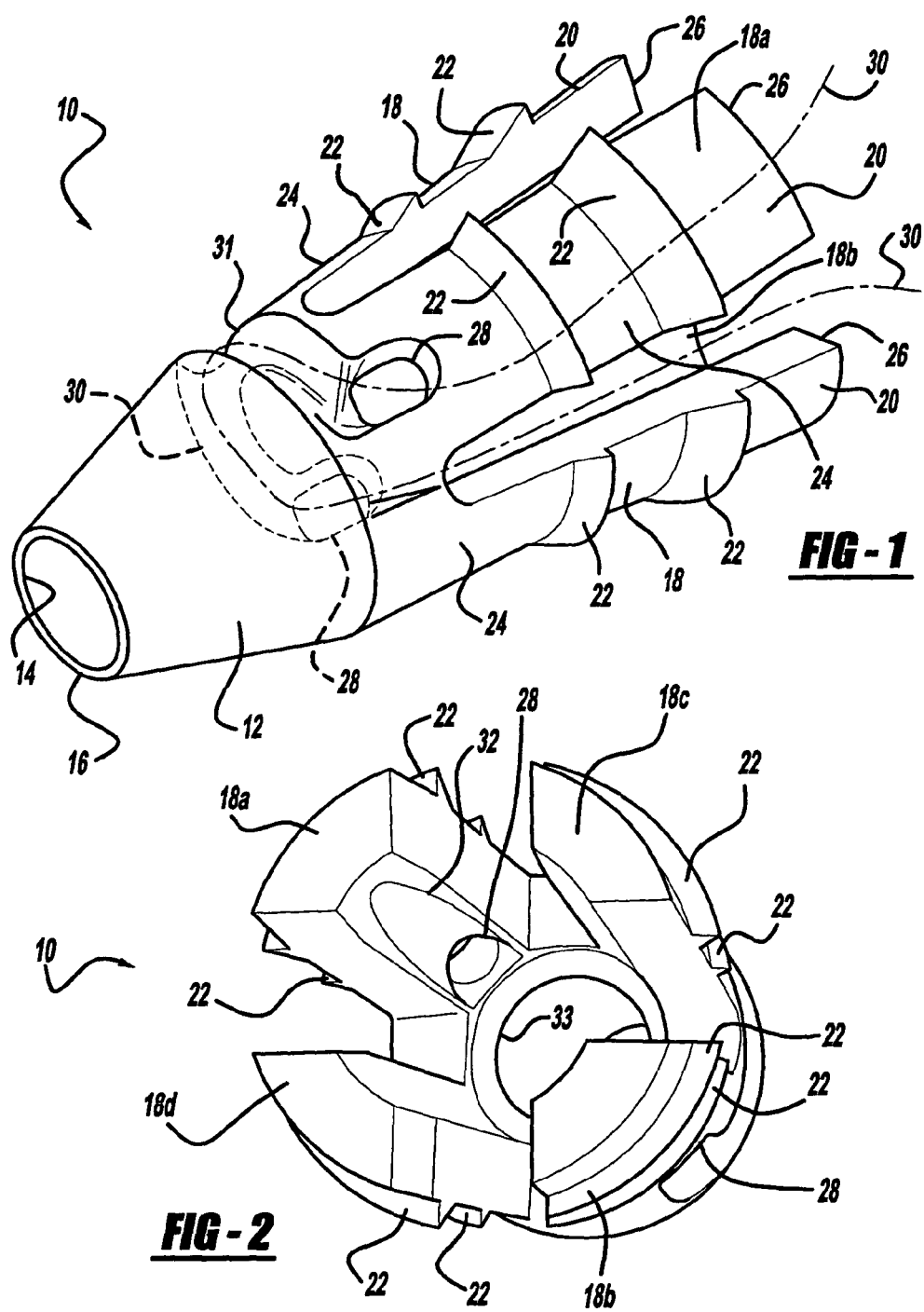

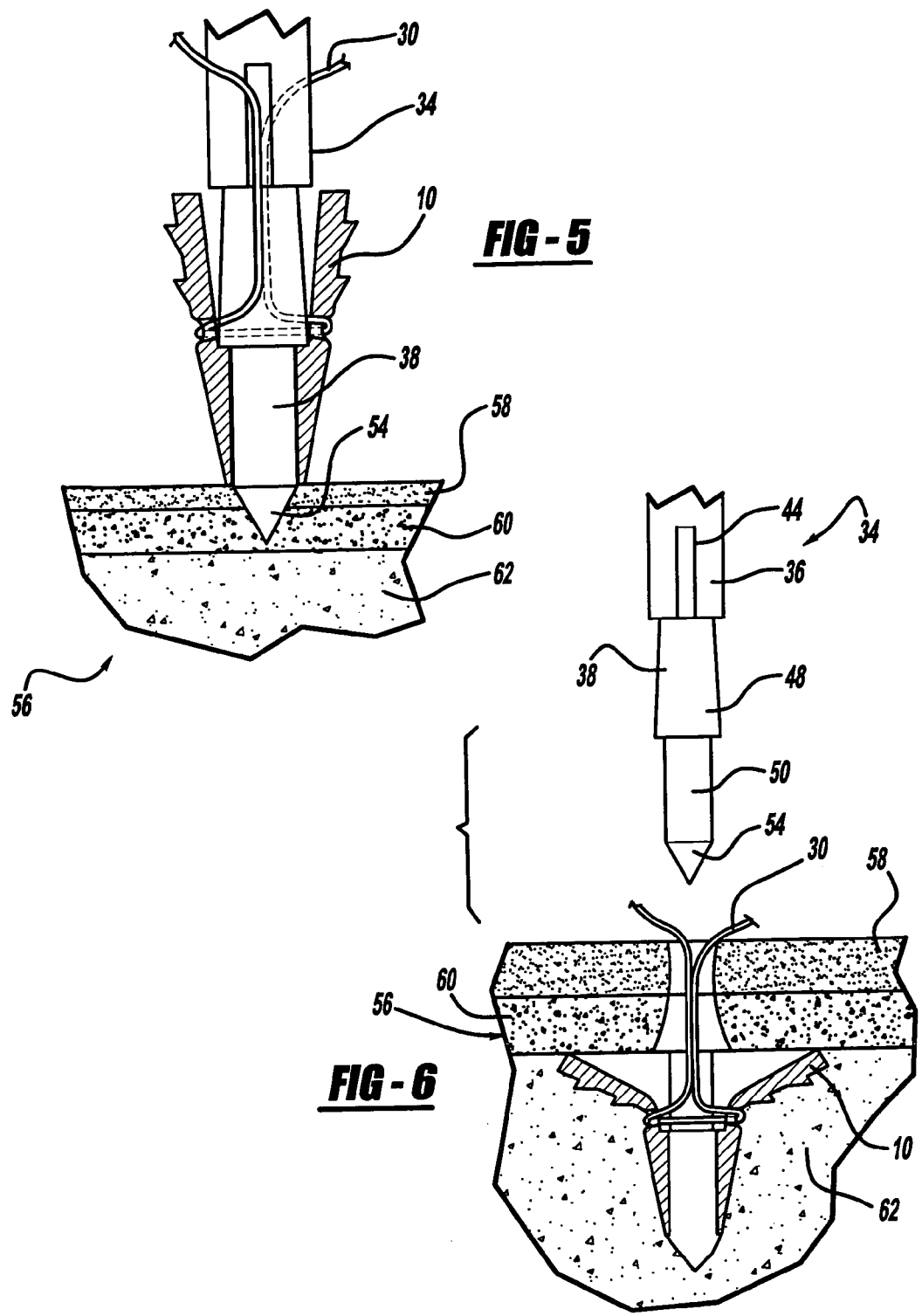

SUTURE ANCHOR

FIELD OF THE INVENTION

The present invention relates generally to an apparatus and method for use in orthopedic surgical procedures. More particularly, the present invention relates to a suture anchor system and a method for securing soft tissues, tendons, and ligaments to bone during orthopedic surgical procedures.

BACKGROUND OF THE INVENTION

It is often necessary to secure soft tissues, tendons and ligaments to bone during orthopedic surgical procedures in both human and animal patients. In the past, various devices and methods have been developed to accomplish such soft tissue attachment. In one procedure, the orthopedic surgeon makes large incisions into the soft tissue to expose the bone, drills angled holes through the bone, and then threads the sutures through the holes in order to achieve ligament or soft tissue attachment. This procedure is complex and time consuming.

Due to the difficulties and potential complications associated with the above procedure, alternate devices and methods have been developed. One such device, developed to overcome some of the disadvantages of the above described device and procedures, is a suture anchor. A suture anchor generally comprises an anchor member that is seated within a bone. A suture strand is secured to the anchor member and, thus, is available for assisting the attachment of soft tissues, tendons, and ligaments to the bone. Suture anchors generally require less complex and time-consuming surgical procedures than those associated with earlier methods for attaching soft tissue to bone.

However, there are improvements that can be made to conventional suture anchors and the surgical procedures used to secure the suture anchor and suture to the bone. It is, therefore, an object of the present invention to provide a suture anchor system and a method for securing soft tissues, tendons, and ligaments to bone during orthopedic surgical procedures, the system may include a resorbable suture anchor that may be implanted within bone without having to pre-drill or tap the bone.

SUMMARY OF THE INVENTION

In one embodiment, the invention provides a resorbable suture anchor operable to hold a suture within a bone. The suture anchor has a cannulated tip that receives a driver during implantation of the anchor, the driver extending from the tip when the anchor is seated on the driver. The anchor further has at least one engagement surface to prevent migration of the anchor from the implantation site. The anchor is made of a resorbable material to permit resorbtion of the anchor within a patient at a desired rate.

In another embodiment, the invention provides a method for implanting a resorbable suture anchor within a bone. The method includes placing the suture anchor having a suture upon a head of a driver such that a tip of the head extends through a cannulated portion of the anchor to expose the tip. The bone is pierced with the tip and the anchor is driven within the bone to a desired position using the driver. The driver is removed from the suture anchor and the bone when the suture anchor is properly positioned within the bone. The suture anchor resorbs within the bone at a desired rate after being driven into the bone.

In another embodiment, the present invention provides for a resorbable suture anchor operable to hold a suture within a bone. The anchor is comprised of a tip, at least two engagement surfaces extending from the tip to prevent migration of the anchor from the bone, and a suture guide extending from the tip between the engagement surfaces and operable to receive and direct the suture toward an interior of the anchor. The suture guide includes a through hole proximate to the tip, a first recessed guide operable to receive the suture extending from the through hole and angled in a first direction, and a second recessed guide operable to receive the suture extending from the through hole and angled in a second direction opposite the first direction. The anchor is made of a resorbable material that permits the resorbtion of the anchor within a patient at a desired rate.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view illustrating exterior features of a suture anchor according to a first embodiment of the present invention;

FIG. 2 is a perspective view illustrating interior features of the suture anchor of FIG. 1;

FIG. 5 is a cross-sectional side view of the implantation of the anchor of FIG. 1 within a bone using the driver of FIG. 3;

FIG. 6 is a cross-sectional side view of the anchor of FIG. 1 seated within a bone after being implanted using the driver of FIG. 3;

DETAILED DESCRIPTION OF THE PREFERRED EMBODIMENTS

Figure 3:
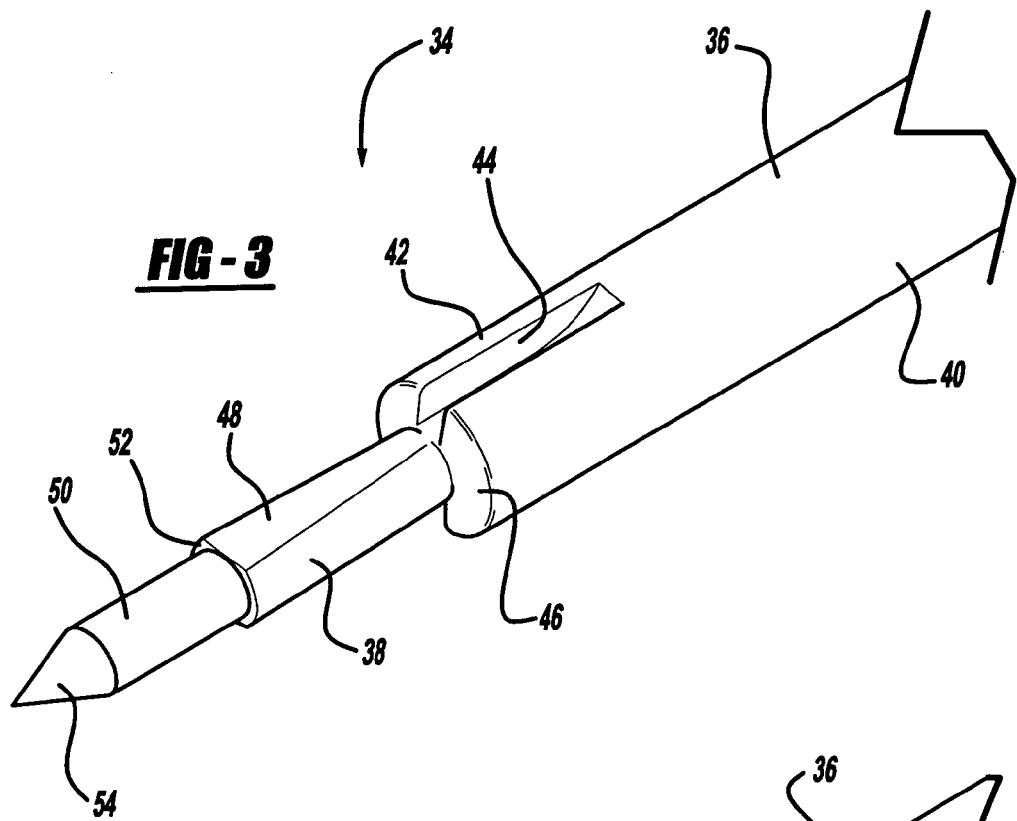
FIG. 3 is a perspective view of a tip region of a suture anchor driver according to the first embodiment.

The following description of the preferred embodiments is merely exemplary in nature and is in no way intended to limit the invention, its application, or uses. Moreover, while the present invention is discussed in detail with securing soft tissue, the present invention may be used to secure any type of graft or implant.

With initial reference to FIG. 1, a suture anchor according to the teachings of an embodiment of the present invention is illustrated at 10. The suture anchor 10 includes a conical head 12 having a cannulation 14 that extends through the head 12 and terminates at an aperture 16. Extending from the conical head 12 opposite the aperture 16 is at least one, but generally four, engagement surfaces, illustrated in the form of wings 18a, 18b, 18c, and 18d. While four wings are illustrated, any number of wings 18 are contemplated. The wings 18 may be flexible and may extend from the head 12 at an angle that diverges from the head 12, such that at a terminal end 20 the wings 18 provide the anchor 10 with a diameter that is greater than a diameter defined by the head 12. Each wing 18 includes at least one rib 22 that rises from an exterior surface 24 of the wings 18. The terminal ends 20 of the wings 18 each include a terminal surface 26 that is preferably angled inward, away from the exterior surface 24.

The wings 18 each have a flex point at the point where the wings 18 transition into the head 12. Both the wing 18a and the wing 18b, located on the opposite side of the anchor 10 from the wing 18a, preferably include an eyelet 28 for receiving a suture strand 30. Extending between the eyelets 28 is a recess 31. The recess 31 is located between the wings 18 and the head 12. The recess 31 is shaped to receive the suture strand 30 and provide sufficient clearance to protect the suture strand 30. In other words, the depth of the recess 31 can substantially accommodate the thickness of the suture strand 30.

The interior of the anchor 10 is illustrated in FIG. 2. As shown in FIG. 2, the interior of the anchor 10 includes a depressed portion 32 that extends along the wing 18a and the wing 18b from the respective eyelets 28. Further, the interior of the anchor 10 includes an annular rim 33 at approximately a point within the head 12 where the wings 18 extend from the head 12.

The anchor 10 may be made from one or more resorbable materials. A variety of resorbable materials known in the art may be used to manufacture the anchor 10. As the anchor 10 does not directly experience impaction forces during implantation (further described below) the anchor 10 may be made from less rigid materials than would normally be required for self-inserting suture anchors. An example of a resorbable material that may be used is LACTOSORB® from Biomet, Inc. of Warsaw, Ind. LACTOSORB® is substantially amorphous (i.e., without crystallinity) and its degradation is uniform. LACTOSORB® is a co-polymer synthesized from all-natural ingredients and is conventionally comprised of 82% L-lactic acid and 18% glycolic acid. However, it must be realized that the particular composition used may vary according to the target tissue, the particular application of the anchor 10, and the rate of resorbtion desired. It shall also be noted that other biocompatible materials may be used.

With reference to FIG. 3, the anchor 10 is implanted using a suitable device, such as a driving instrument 34. The driving instrument 34 generally includes a handle 36 and a head 38. The handle 36 includes a first end 40 and a second end 42 opposite the first end 40. The second end 42 includes two wells 44 (only one well 44 is shown) positioned within the handle 36 opposite each other. The second end 42 terminates at a planar end portion 46. The head 38 extends from the planar end portion 46.

The head 38 includes a first head portion 48 extending from the planar end portion 46 and a second head portion 50 extending from the first head portion 48. A planar perimeter edge 52 of the second head portion 50 is exposed at the point where the first head portion 48 meets the second head portion 50. The second head portion 50 terminates at a tip 54.

Figure 4:
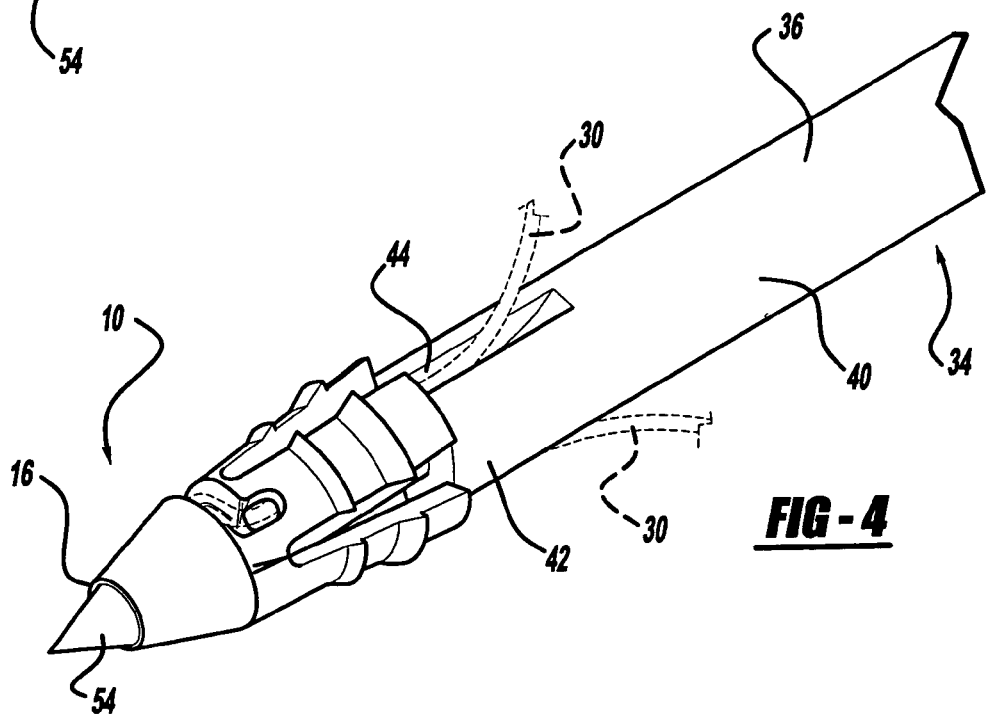
FIG. 4 is a perspective view illustrating cooperation between the suture anchor of FIG. 1 and the driver of FIG. 3.

With reference to FIG. 4, the cooperation between the driving instrument 34 and the anchor 10 will now be described. Before the anchor is seated upon the driving instrument 34, the suture 30 is threaded through the eyelets 28. Specifically, one end of the suture 30 is inserted within an interior of the anchor and threaded through one of the eyelets 28. The suture 30 is then directed through the recess 31 and back to the interior of the anchor 10 through the opposite eyelet 28. With the suture 30 threaded though the eyelets 28, the anchor 10 is seated upon the head 38 of the anchor 10, such that the tip 54 extends through the aperture 16 and the planar perimeter edge 52 abuts the annular rim 33 within the anchor 10. To prevent the suture 30 from being pinched between the anchor 10 and the driving instrument 34, the portions of the suture 30 that extend from the anchor 10 are positioned within the wells 44. The depressed portions 32 of the wings 18 help to align the suture 30 within the anchor 10 so that the suture 30 is properly directed through the wells 44.

With reference to FIG. 5, implantation of the anchor 10 within a bone 56 of a patient will now be described. With the anchor 10 seated upon the head 38 of the driving instrument 34, the anchor 10 is driven through a soft tissue layer 58 and a cortical layer 60 of the bone 56, the tip 54 piercing the tissue 58 and bone 56 rather than the anchor 10 itself. As the anchor 10 passes through the cortical layer 60 the wings 18 compress inward, towards the interior of the anchor 10. The anchor is then driven further into cancellous layer 62 of the bone 56. The cancellous layer 62 of the bone 56 is softer than the cortical layer 60. As a result, once the anchor enters the cancellous layer 62 the wings 18 expand again to their natural state. The terminal surface 26 of the wings 18 contact an undersurface of the cortical layer 60 to secure the anchor 10 within the cancellous layer 62. The ribs 22 further prevent migration of the anchor 10 by engaging the cancellous layer 62.

With reference to FIG. 6, to better secure the anchor 10 within the bone 56 and prevent migration of the anchor 10, the wings 18 may be expanded such that they extend from the anchor 10 at approximately a right angle to the head 12. The wings 18 may be expanded using a modified driver 34 or any other suitable instrument. After the anchor 10 is in position, the sutures are then secured to the soft tissue 58 to secure the soft tissue 58 in place.

In addition to the embodiment of the anchor 10 discussed above, it will be appreciated that the anchor 10 may include various additional aspects and features. For example, the suture strand 30 may be molded within the anchor 10, thus eliminating the need for the eyelets 28 and the recess 31.

Figure 7:
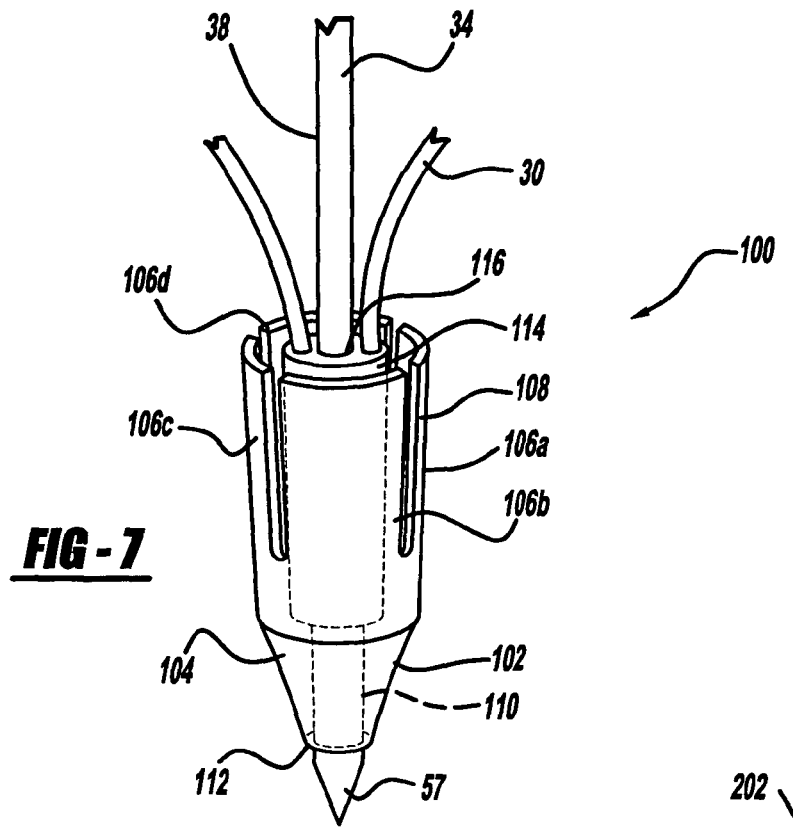
FIG. 7 is a perspective view of a suture anchor illustrated according to a second embodiment of the present invention.

With reference to FIG. 7, a suture anchor according to an additional embodiment of the present invention is illustrated at 100. FIG. 7 illustrates the anchor 100 seated upon the head 38 of the driving instrument 34, leaving the tip 54 of the instrument 34 exposed so that the instrument 34, not the anchor 100, bears the load during the implantation procedure. The anchor 100 includes a conical head 102, at a first end 104 of the anchor 100, and four flexible wings 106a through 106d extending from the conical head 102 to a second end 108 that is opposite the first end 104. The wings 106 extend from the head 102 at an angle to provide the anchor 100 with a diameter at the second end 108 that is greater than the diameter at the first end 104. The wings 106 may optionally include a series of ribs (not shown) to help prevent migration of the anchor 100 from its implanted position. Extending through the conical head 102 is a cannulation or through bore 110. The cannulation 110 terminates at the first end 104 at a first aperture 112, through which the tip 54 of the driving instrument 34 extends when the anchor 100 is seated upon the instrument 34.

From the head 102 the cannulation 110 extends to the second end 108 through a center body 114. The center body 114 terminates at the second end 108 at a second aperture 116. The second aperture 116 receives the tool 34. The second end 108 of the center body 114 also receives the suture strand 30. The suture strand 30 may either be molded within the center body 114 (as illustrated in FIG. 7) or may be inserted through eyelets of the center body 114 (not shown).

The anchor 100 is preferably made from a suitable resorbable material. The anchor may be made entirely of a single resorbable material or of varying types of different resorbable materials. For example, the head 102 may be made of a first resorbable material while the remaining portion of the anchor 100 may be made of a second resorbable material that is different than the first resorbable material. Because the head 102 does not bear the force of impaction during implantation of the anchor 100, the head 102 may be made from a resorbable material that is less rigid than is normally required of self-inserting suture anchors. The anchor 100 is preferably made of LACTOSORB® from Biomet, Inc. of Warsaw, Ind. LACTOSORB® is substantially amorphous (i.e., without crystallinity) and its degradation is uniform. LACTOSORB® is a co-polymer synthesized from all-natural ingredients and is conventionally comprised of 82% L-lactic acid and 18% glycolic acid. However, it must be realized that the particular composition used may vary according to the target tissue, the particular application of the anchor 100, and the rate of resorbtion desired.

Using the driving instrument 34, the suture anchor 100 is implanted within the bone 56 in a manner substantially identical to the implantation of the suture anchor 10 using the driving instrument 34, the driving instrument 34 absorbing the force of impaction rather than the anchor 100 as it is the driving instrument 34 that pierces the bone 56 rather than the anchor 100. Thus, the above description of the implantation of the suture anchor 10 using the driving instrument 34 equally applies to the implantation of the suture anchor 100 using the driving instrument 34, and need not be repeated here.

Figure 8:
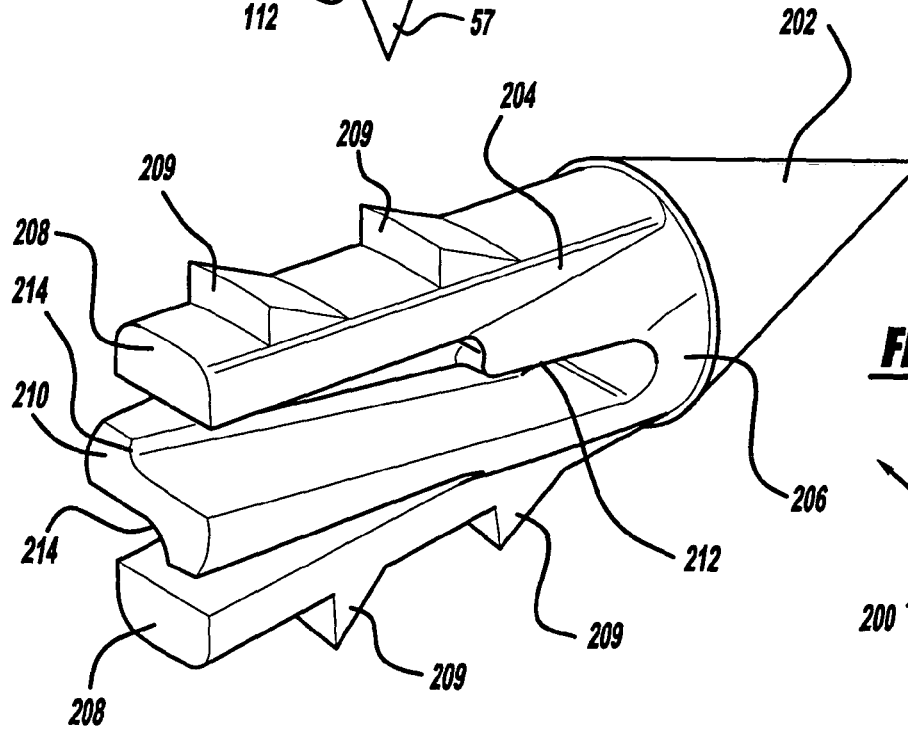
FIG. 8 is a perspective view of a suture anchor illustrated according to a third embodiment of the present invention.

With reference to FIG. 8, a suture anchor according to an additional embodiment of the present invention is illustrated at 200. The suture anchor 200 includes a conical, pointed tip 202 and a body 204. Neither the body 204 nor the pointed tip 202 are cannulated. The body 204 includes a base 206. Extending from the base 206, away from the pointed tip 202, are at least one, but generally two, flexible wings 208. The wings 208 extend from the base 206 at an angle, causing the diameter of the anchor 200 to be smaller at the base 206 than at an end portion of the wings 208 opposite the base 206. The wings 208 may include raised ribs 209 to further prevent the anchor 200 from migrating from its intended position.

Extending from the base 206, between the wings 208, is a suture guide 210. Extending through the suture guide 210, at a point near the base 206, is a through hole 212. Extending along opposite sides of the suture guide 210, from the through hole 212, are recesses 214. The recesses 214 are each angled, in opposite directions, toward an interior of the anchor 200.

The suture strand 30 is threaded through the through hole 212 and seated within each of the recesses 214. The recesses 214 direct the suture strand 30 toward the interior of the anchor 200. By angling the suture 30 towards the interior of the anchor 200, the suture guide 210 protects the suture 30 from possible damage during implantation.

Figure 9:
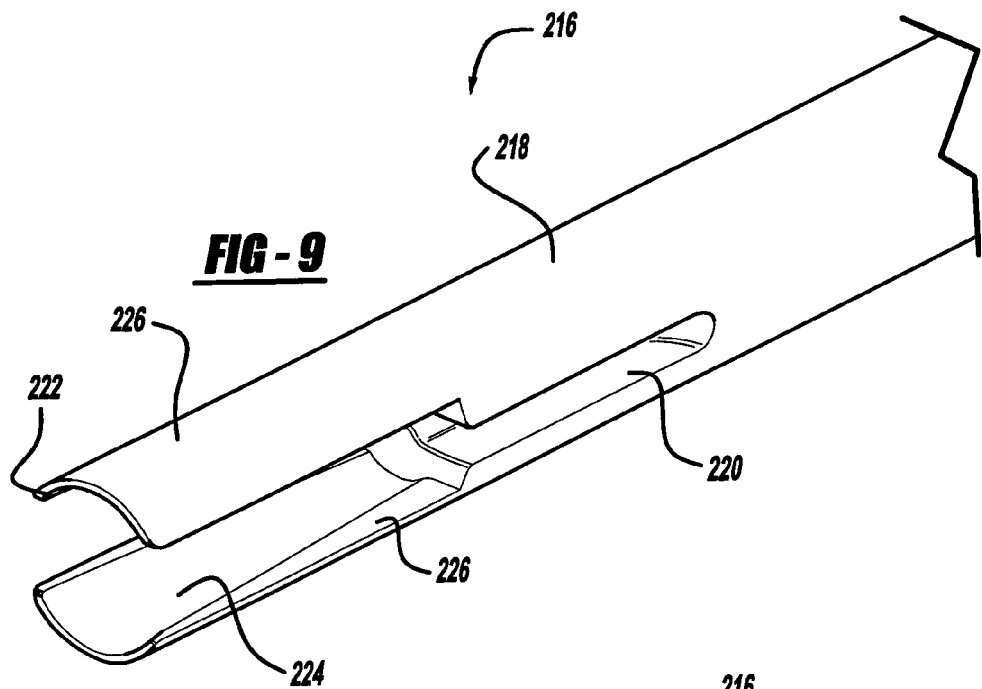
FIG. 9 is a perspective view of a tip region of a suture anchor driver illustrated according to the second embodiment of the present invention.

With reference to FIG. 9, an implantation tool 216 for implanting the anchor 200 is illustrated. The implantation tool 216 includes a proximal end (not shown) and a distal end 218, the distal end 218 being located opposite the proximal end. The distal end 218 includes two depressions 220 positioned on opposite sides of the tool 216. At a terminus 222 of the distal end 218 is an aperture 224. The aperture 224 is defined by two extensions 226. Between the two extensions are two side slits that extend to the depressions 220.

Figure 10:
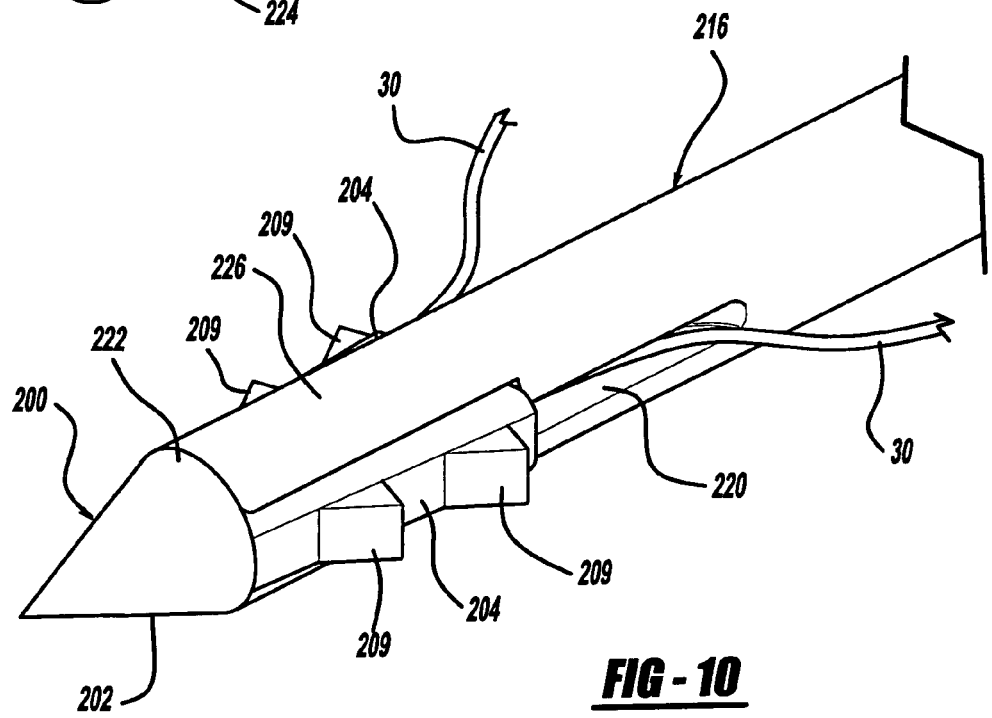
FIG. 10 is a perspective view illustrating cooperation between the suture anchor of FIG. 8 and the driver of FIG. 9.

As seen in FIG. 10, the anchor 200 is seated within the aperture 224 such that the wings 208 extend within and through the side slits defined by the extensions 226 and the pointed tip 202 is left exposed at the terminus 222. After the anchor 200 is seated within the tool 216, the suture 30 secured to the anchor 200 is positioned so that it extends from the anchor 200, through the depressions 220, and out from the implantation tool 216. The anchor 200 is retained within the tool 216 due to the frictional forces between the anchor 200 and the tool 216.

The anchor 200 is made from a suitable resorbable material. The anchor 200 may be made entirely of a single resorbable material or of varying types of different resorbable materials. For example, the tip 202 may be made of a first resorbable material while the remaining portion of the anchor may be made of a second resorbable material, the first resorbable material being different than the second material and preferably harder than the second material to permit the tip 202 to withstand forces exerted upon the tip 202 during implantation. One type of resorbable material that may be used is LACTOSORB® L15 from Biomet, Inc. of Warsaw, Ind. LACTOSORB® L15 is typically comprised of 85% L-lactic acid and 15% glycolic acid. As LACTOSORB® L15 is harder than standard resorbable materials, it is preferably used within the tip 202.

In addition to the embodiment of the anchor 200 discussed above, it will be appreciated that the anchor 10 may include various additional aspects and features. For example, the suture strand 30 may be molded within the anchor 200 itself, thus eliminating the need for the through hole 212.

Figure 11:
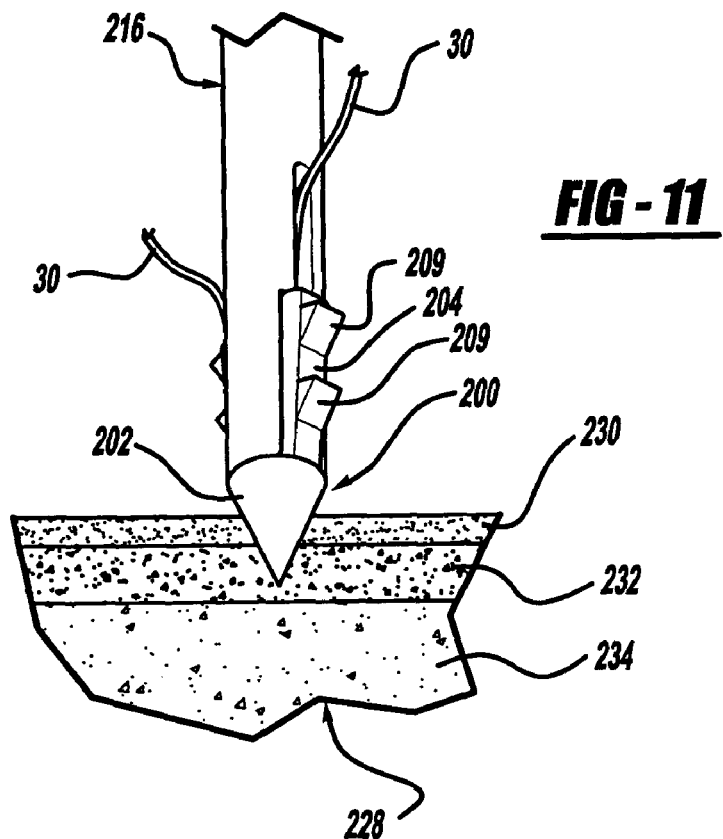
FIG. 11 is a perspective view of cross-sectional side view of the anchor of FIG. 8 being implanted within a bone using the driver of FIG. 9.
Figure 12:
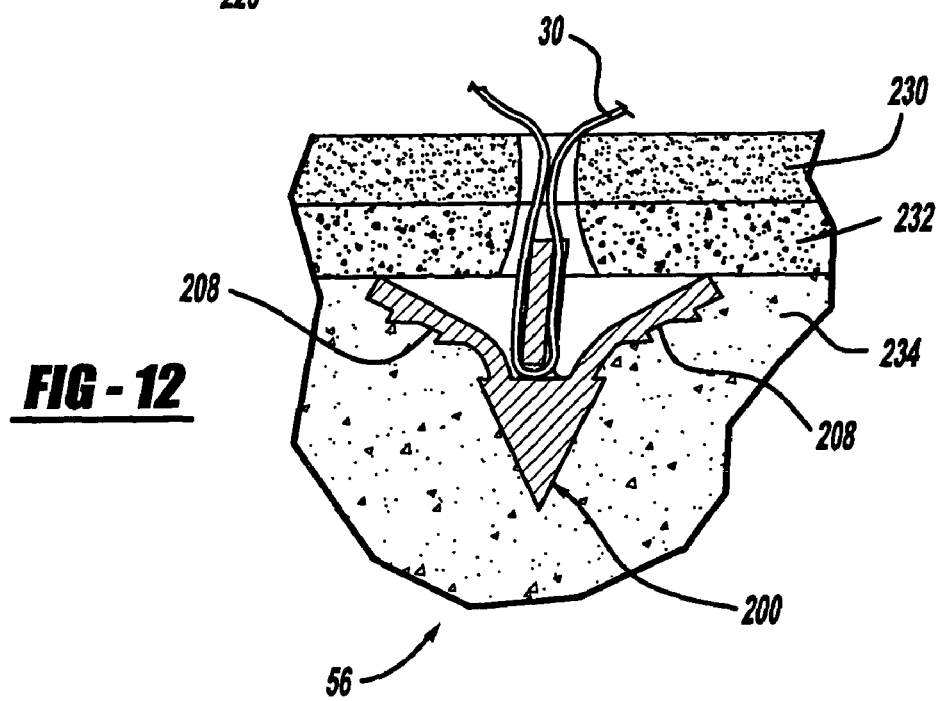
FIG. 12 is a cross-sectional side view of the anchor of FIG. 8 seated within a bone after being implanted using the driver of FIG. 9.

With reference to FIGS. 11 and 12, implantation of the anchor 200 within a bone 228 of a patient will now be described. With the anchor 200 seated within the terminus 222 of the implantation tool 216, and the pointed tip 202 exposed and extending from the tool 216, the anchor 200 is implanted into the bone 228. Unlike the anchor 10 and the anchor 100 described above, the anchor 200 pierces the bone 228, not the driving instrument 34 or the implantation tool 216. The anchor 100 may be self-inserting (i.e. self-tapping, self-drilling, or self-punching). Using the tool 216, the anchor 200 is driven through a soft tissue layer 230 and a bone cortical layer 232 and seated within a bone cancellous layer 234. As the anchor 200 passes through the cortical layer 232 the wings 208 compress inward towards the suture guide 210. After the anchor 200 enters the cancellous layer 234 the wings 208 expand back to their original position and contact the cortical layer to prevent the anchor 200 from migrating out of the bone 228. To further prevent the anchor 200 from migrating from the bone 228, the wings 208 can be opened such that the wings 208 extend from the anchor 200 at up to approximately a right angle to the base 206.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A suture anchor operable to hold a suture within a bone comprising:
   a tip;
   a longitudinal axis of said anchor that extends through a center of said tip;
   a first flexible wing with retention features thereon, said first flexible wing extends from said tip;
   a second flexible wing with retention features thereon, said second flexible wing extends from said tip and is opposite to said first flexible wing;
   a center plane that extends through said longitudinal axis from said first flexible wing to said second flexible wing; and
   a suture guide between said first flexible wing and said second flexible wing that extends from said tip along said longitudinal axis and is operable to receive and direct said suture toward an interior of said anchor, said suture guide includes:
      a through hole proximate to said tip, said through hole extends through said longitudinal axis and includes a center axis that is perpendicular to said longitudinal axis;
      a first recessed guide operable to receive said suture, said first recessed guide extends from said through hole and is angled in a first direction, said first recessed guide extends across said center plane; and
      a second recessed guide operable to receive said suture, said second recessed guide extends from said through hole and is angled in a second direction opposite to said first direction, said second recessed guide extends across said center plane.

2. The suture anchor of claim 1, wherein said anchor comprises 85% L-lactic acid and 15% glycolic acid.

3. The suture anchor of claim 1, wherein said tip is self-inserting.

4. The suture anchor of claim 1, wherein said tip is solid.

5. The suture anchor of Claim 1, wherein said anchor is seated within a driver during implantation of said anchor, said driver having two depressions to receive said anchor and protect said anchor during implantation of said anchor.

6. The suture anchor of claim 1, wherein said tip is comprised of a first resorbable material, said first and said second flexible wings are comprised of a second resorbable material, and said suture guide is comprised of a third resorbable material, said first resorbable material being harder than said second and said third resorbable materials.

7. The suture anchor of claim 6, wherein said second resorbable material and said third resorbable material are at least substantially similar.

8. The suture anchor of claim 1, wherein said suture anchor is resorbable.

9. The suture anchor of claim 1, wherein said suture anchor comprises only two of said flexible wings positioned 180° apart.

10. A method for implanting a resorbable suture anchor and a suture within a bone comprising:
   inserting the suture within a suture retention portion of the suture anchor, the suture retention portion located between first and second winged engagement surfaces that extend from a tip of the suture anchor;
   positioning the suture on the suture retention portion such that the suture extends:
      through a hole in said suture retention portion having a center axis that is perpendicular to a longitudinal axis extending through a center of the tip;
      along a first angled recess; and
      along a second angled recess, said first angled recess is spaced apart from said second angled recess, and both of said first angled recess and said second angled recess are angled in opposite directions and extend across a plane that extends from said first winged engagement surface to said second winged engagement surface and along the longitudinal axis of the suture anchor;
   placing said suture anchor having the suture within an implantation tool such that said tip and a portion of each of said first and said second winged engagement surfaces protrude from said implantation tool;
   piercing a bone with said tip of said suture anchor;
   driving said anchor within said bone to a desired position using said implantation tool;
   removing said implantation tool from said suture anchor and said bone when said suture anchor is properly positioned within said bone; and
   securing said anchor within said bone by extending the first and the second winged engagement surfaces;
   wherein said suture anchor resorbs within said bone at a desired rate after being driven into said bone; and
   wherein the tip is comprised of a first resorbable material, the first and the second engagement surfaces are comprised of a second resorbable material, and the suture retention portion is comprised of a third resorbable material, the first resorbable material is harder than the second and the third resorbable materials.

* * * * *